US010966817B2

(12) United States Patent
Otts (10) Patent No.: US 10,966,817 B2
(45) Date of Patent: Apr. 6, 2021

(54) OPEN, SEAL-LESS INTRAOCULAR LENS

(71) Applicant: Verily Life Sciences LLC, Mountain View, CA (US)

(72) Inventor: Daniel B. Otts, Pleasanton, CA (US)

(73) Assignee: Verily Life Sciences LLC, South San Francisco, CA (US)

(*) Notice: Subject to any disclaimer, the term of this patent is extended or adjusted under 35 U.S.C. 154(b) by 699 days.

(21) Appl. No.: 15/695,746

(22) Filed: Sep. 5, 2017

(65) Prior Publication Data

US 2018/0092740 A1 Apr. 5, 2018

Related U.S. Application Data

(60) Provisional application No. 62/403,796, filed on Oct. 4, 2016.

(51) Int. Cl.
*A61F 2/16* (2006.01)
*G02B 26/00* (2006.01)
*G02C 7/08* (2006.01)

(52) U.S. Cl.
CPC .......... *A61F 2/1624* (2013.01); *A61F 2/1601* (2015.04); *A61F 2/1613* (2013.01); *A61F 2/1635* (2013.01); *G02B 26/005* (2013.01); *G02C 7/085* (2013.01); *A61F 2/1627* (2013.01); *A61F 2/1648* (2013.01); *A61F 2/1675* (2013.01); *A61F 2002/16905* (2015.04); *A61F 2210/0076* (2013.01); *A61F 2250/0001* (2013.01); *A61F 2250/0002* (2013.01);
(Continued)

(58) Field of Classification Search
CPC .... A61F 2/1601; A61F 2/1613; A61F 2/1624; A61F 2/1635; A61F 2/1648; A61F 2/1675; A61F 2250/0053; G02B 26/005; G02C 7/085
See application file for complete search history.

(56) References Cited

U.S. PATENT DOCUMENTS

| 2012/0245444 A1 | 9/2012 | Otis et al. |
| 2014/0002789 A1 | 1/2014 | Pugh et al. |
| 2014/0002790 A1 | 1/2014 | Pugh et al. |

(Continued)

FOREIGN PATENT DOCUMENTS

| WO | 2007107589 A1 | 9/2007 |
| WO | 2012061411 A1 | 5/2012 |

(Continued)

OTHER PUBLICATIONS

PCT/US2017/053756, International Search Report and Written Opinion of the International Searching Authority, dated Jan. 2, 2018, 16 pages.

*Primary Examiner* — William H Matthews
(74) *Attorney, Agent, or Firm* — Christensen O'Connor Johnson Kindness PLLC (57) ABSTRACT

An open, seal-less intraocular lens is disclosed herein. An example intraocular lens may include an annular substrate including an oil electrode disposed in or on an inner sidewall of the annular substrate to electrostatically manipulate a volume of electrowetting oil, an optical window coupled to the substrate, where a side of the optical window adjacent to the inner sidewall and the inner sidewall of the annular substrate define a region for constraining the volume of electrowetting oil, and a saline electrode coupled to the annular substrate, the saline electrode positionable within an aqueous humor of an eye upon implantation

17 Claims, 7 Drawing Sheets

(52) U.S. Cl.
   CPC ............. *A61F 2250/0091* (2013.01); *A61F 2250/0092* (2013.01); *A61F 2250/0096* (2013.01)

(56) References Cited

U.S. PATENT DOCUMENTS

2014/0343387 A1  11/2014  Pugh et al.
2015/0359626 A1  12/2015  Caffey et al.

FOREIGN PATENT DOCUMENTS

OPEN, SEAL-LESS INTRAOCULAR LENS

CROSS REFERENCE TO RELATED APPLICATION

This application claims the benefit of U.S. Provisional Application No. 62/403,796 filed on Oct. 4, 2016, the contents of which are incorporated herein by reference.

TECHNICAL FIELD

This disclosure relates generally to implantable ophthalmic devices, and in particular but not exclusively, relates to implantable intraocular lenses.

BACKGROUND INFORMATION

Implantable optical devices may be constrained in size by conventional surgical techniques. For example, eye incisions may desirably be limited to mm length incisions, 2 to 5 mm for example. The small incisions, however, may preclude or limit the implantation of bulky ophthalmic devices, or at least cause the physician to limit their recommendation. As such, implantation of intraocular devices that include multiple components and electronics may be limited due to their bulkier size over conventional intraocular devices. While fabrication techniques may allow some reduction in size of such intraocular devices, the manipulation of the devices during implantation, such as folding and/or rolling, may promote undesirable failure mechanisms. As such, it may be desirable to provide an intraocular device that includes multiple components and electronics having reduced volume and that can withstand surgical manipulation.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. Not all instances of an element are necessarily labeled so as not to clutter the drawings where appropriate. The drawings are not necessarily to scale, emphasis instead being placed upon illustrating the principles being described.

DETAILED DESCRIPTION

Embodiments of a system and method for implantable intraocular lenses (IOLs) having an open, seal-less construction are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Smart" intraocular lenses (IOLs) are implantable ophthalmic devices that include electronics that perform a variety of tasks. For example, some smart IOLs may include dynamic optics that provide accommodation to a user. The dynamic optic may be based on liquid crystal (LC) or electrowetting techniques, for example. LC-based IOLs may include one or more layers of LC-material contained between optical elements that may include electrodes and diffractive optics, for example. The LC-based IOLs, as such, require a protective enclosure to contain the LC-material within the IOL and to prevent leakage into the user's eye. IOLs based on electrowetting techniques likewise are conventionally encased in an enclosure. The electrowetting IOLs further included two immiscible liquids, such as an oil and a saline, that provide a dynamic optic via a deformable refractive interface formed between the two liquids. In addition to the dynamic optic components, both types of IOLs further include electronics and power sources that control and power the dynamic optic. Accordingly, the IOLs, in at least part due to the dynamic optic and the controlling electronics, may become somewhat bulky, especially compared with conventional static IOLs.

The implantation of the IOLs may put constraints on their size, area and/or volume, however. Conventional static IOLs may be implanted using incisions that range from 2 to 5 mm in length (based on current surgical techniques), but bulkier IOLs may not fit through a 5 mm incision. As such, eye care physicians may be less inclined to use them. Further, if the IOLs are folded and/or rolled up to fit through an incision that is 5 mm or less in length, the process of folding/rolling and unfolding/unrolling may cause defects and/or device failure. For example, electronic interconnects may be damaged or broken leading to device failure. Or, an IOL enclosure may burst allowing the exchange of fluids between the eye and the device, which may lead to malfunction or failure of the IOL. Accordingly, it may be desirable for IOLs to be small enough and malleable enough to conform to current surgical techniques, and which may be resistant to various failure mechanisms due to being folded and/or rolled.

One solution may be an IOL based on electrowetting techniques that uses a single refractive lens, no enclosure, and where the eye's aqueous humor, for example, is the saline-like fluid. The IOL may be implanted and positioned as desired in the eye, then a precise amount of oil may be injected into place behind the single lens and in contact with an oil electrode. The oil may be attracted to one or more surfaces of the IOL including a surface of the oil electrode, which may assist with containing the oil in a desired location. A saline electrode may be placed elsewhere in the eye as long as it is in contact with the aqueous humor. An interface between the oil and the aqueous humor may provide a deformable refractive optic, e.g., a dynamic optic. As such, a voltage may be produced across the oil-aqueous humor interface between the oil electrode and the saline electrode to change a shape of the interface, which may change an optical power of the deformable refractive optic.

Figures 1A, 1B:
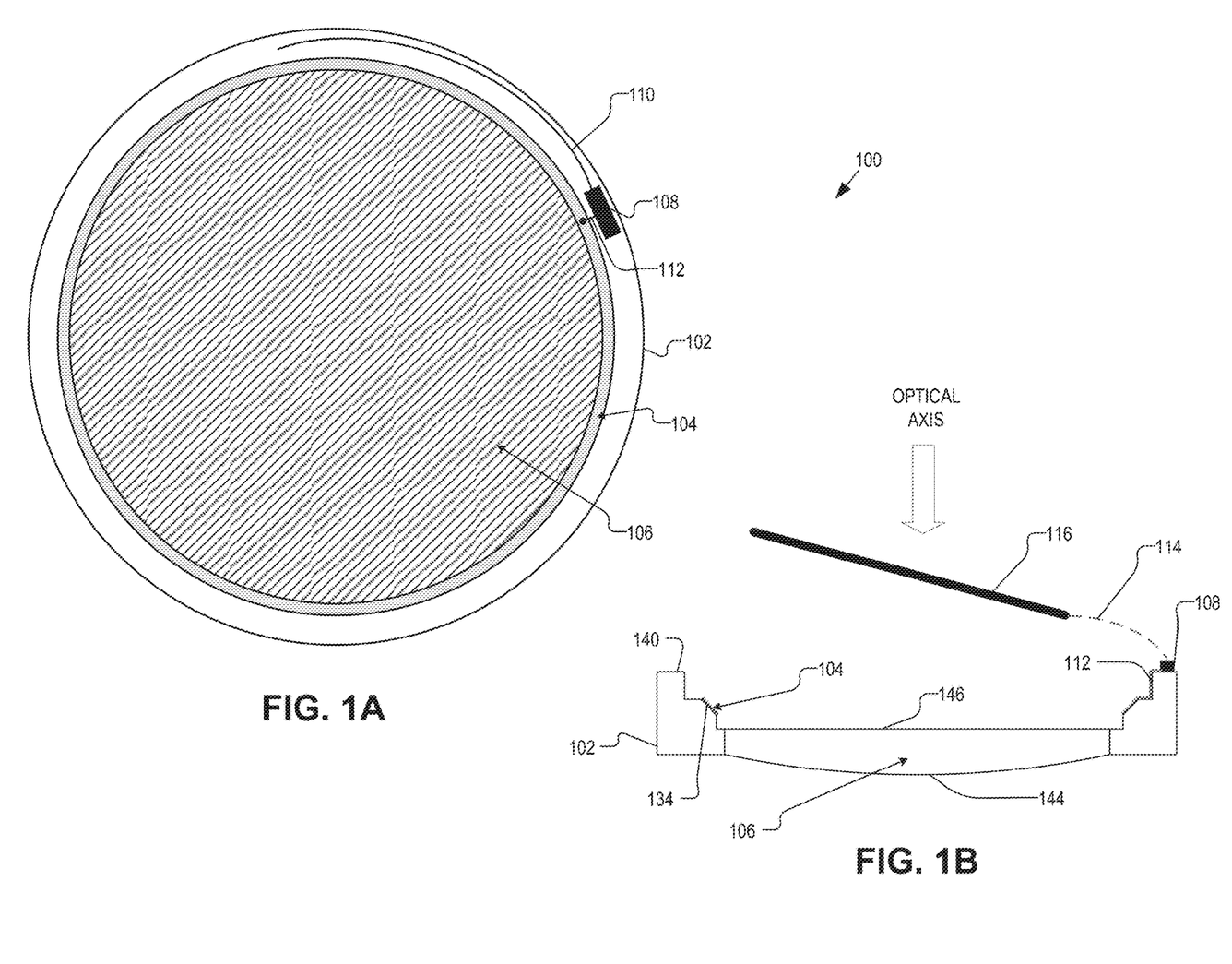
FIGS. 1A and 1B are a plan view illustration of an intraocular lens (IOL) and a side view illustration of the IOL, respectively, having an open, seal-less construction in accordance with an embodiment of the present disclosure.

FIGS. 1A and 1B are a plan view illustration of an intraocular lens (IOL) 100 and a side view illustration of the IOL 100, respectively, having an open, seal-less construction in accordance with an embodiment of the present disclosure. The IOL 100 may be implanted into a user's eye to provide accommodation to the user. For example, the IOL 100 may be implanted to treat the user for cataracts or for presbyopia, which occurs prior to the formation of cataracts. The IOL 100 may provide accommodation using a dynamic optic. In some embodiments, the dynamic optic may be based on an electrowetting technique with an interface between an electrowetting oil and the aqueous humor of the eye, where the interface forms a deformable refractive optic, e.g., the dynamic optic.

The illustrated embodiment of the IOL 100 includes a substrate 102, an oil electrode 104, an optical window 106, control electronics 108, an antenna 110, a first interconnect 112, a second interconnect 114, and a saline electrode 116. The first interconnect 112 may be one or more interconnects disposed on the substrate 102 that couple the control electronics 108 with the oil electrode 104. The control electronics 108 may additionally be coupled to the saline electrode 116 via the second interconnect 114. The control electronics 104 may provide one or more control signals, voltages for example, to the oil and saline electrodes 104, 116, respectively, to induce an electrowetting operation of the IOL 100, which may use an electrowetting oil (not shown) and a saline or the aqueous humor of an eye to form the refractive interface of the dynamic optic.

The substrate 102 may be annular shaped and have an aperture, e.g., opening, formed through a middle diameter. An inner sidewall 134 of the substrate 102 may at least partially define the aperture. In some embodiments, the inner sidewall 134 may be at an oblique angle to a top or bottom surface of the substrate 102, such as surface 140. For example, the inner sidewall may be at a 45-degree angle to the surface 140 of the substrate 102. Further, the inner sidewall 134 may have the form/shape of a conical frustum. In some embodiments, the conical frustum may be at 45-degrees. The angle of the sidewall 134, however, is not a limiting aspect of the present disclosure, and may be formed at other angles depending on various vision and eye parameters of an end user. The substrate 102 may be formed from a soft, flexible, deformable, biocompatible material, such as a silicone gel, Acrysof, or other soft, foldable polymers. In some embodiments, the annular shape of the substrate 102 may have a diameter of about 10 millimeters, a radial width of about 1 millimeter (e.g., an outer radius 1 millimeter larger than an inner radius), and a thickness of about 50 micrometers.

The oil electrode 104, which may also be referred to as a sidewall electrode, may be disposed on the inner sidewall 134 of the substrate 102. In some embodiments, the oil electrode may include a thin conductive film disposed on the inner sidewall 134, and one or more dielectric layers disposed over the thin conductive film. An exposed surface of the oil electrode 104 may be hydrophobic and wettable by an electrowetting oil (not shown) in the presence of aqueous fluids, e.g., saline or the aqueous humor of the eye. Additionally, the thin conductive film may be coupled to the first interconnect 112, which may also be, at least partially, coated by the one or more dielectric layers. The thin conductive film may be transparent or semi-transparent and formed from a conductive polymer or a nanowire mesh, for example. The first interconnect 112 may be formed from the same material(s) as the thin conductive film, or different conductive materials, gold, silver, or platinum for example. In some embodiments, the first interconnect may be formed from an inert, biocompatible conductor. The one or more dielectric layers may be formed from parylene (parylene-C, parylene-D, etc.), aluminum oxide, or Teflon AF1600, to name a few examples, but these examples should not be considered limiting.

The optical window 106 may be coupled to the substrate 102 and at least span the aperture. The optical window 106 may optionally provide a static optical power, and may have any lens shape desired. For example, the optical window 106 may be a plano-convex lens as shown in FIG. 1B, but other shapes are also contemplated, such as plano-plano, convex-convex, concave, convex, and convex-convex, to name a few. It should be noted, however, that the shape of the optical window is a non-limiting aspect of the present disclosure. The optical window 106 may be formed from the same or a different material as the substrate 102. In general, it may be desirable that the optical window 106 be deformable, e.g., rollable, foldable, etc., but capable of returning to a desired geometry upon unrolling/unfolding. As such, a thickness of the optical window 106 may be so that the desired geometry is obtained upon unrolling/unfolding without kinks, folds, bends, etc., remaining in the optical window 106. In some embodiments, the substrate 102 and the optical window 106 may be integrated into a single component.

The saline electrode 116 may be disposed anywhere in the eye that allows contact with the aqueous humor, and may not need to be adjacent to or proximate an electrowetting oil-saline/aqueous humor interface. The saline electrode 116 may be formed from an inert metal, such as gold or platinum, and may provide charge to the saline/aqueous humor fluid of the electrowetting lens.

The control electronics 108 may be disposed on the surface 140 of the substrate 102. In some embodiments, the control electronics 108 may include control logic, one or more power supplies, e.g., batteries and/or super capacitors, and communication electronics. The control electronics 108 choreograph the operation of the IOL 100, for example, by determining when to cause the IOL to provide accommodation and by how much. For example, the control electronics 108 may establish a potential difference between the oil electrode 104 and the saline electrode 116, which may cause the oil-saline/aqueous humor interface to change shape. The changing shape of said interface may provide a change in optical power, for example.

The control electronics 108 may be coupled to the oil electrode via the first interconnect 112, and coupled to the saline electrode 116 via the second interconnect 114. The second interconnect 114 may be a wired or wireless interconnect, for example. The first interconnect 112 may be disposed on one or more surfaces of the substrate 102 that separate the control electronics 108 from the oil electrode 104.

It should be noted that the IOL 100 may differ from conventional IOLs in that the IOL 100 is open to the interior of the eye and is not sealed inside of an enclosure, e.g., a seal-less construction. As such, all external and exposed surfaces of the IOL 100 may be in contact with the aqueous humor of the eye after implantation. Additionally, the electrowetting oil may not be disposed on the posterior side 146 of the optical window 106 until after the IOL 100 has been implanted. After implantation, which will be discussed in more detail below, a desired amount of electrowetting oil may be dispensed, by a needle for example, onto the posterior side 146 of the optical window 106. The electrowetting oil may wet the oil electrode 104 and the posterior side 146. Due to the attraction of the electrowetting oil to at least the oil electrode 104, and the immiscibility of the electrowetting oil and saline and/or aqueous humor, the electrowetting oil may remain on/adjacent to the posterior side 146 of the optical window 106 and the oil electrode 104.

The interface of the electrowetting oil and saline and/or aqueous humor may form the deformable refractive lens of the IOL 100, which may be deformed due to a potential difference between the oil electrode 104 and the saline electrode 116. For example, by charging the oil electrode 104, an outer surface of the oil electrode 104 may become more or less attractive to the electrowetting oil, which may cause the shape of the electrowetting oil spanning the aperture to change. The change in shape may change the shape of the electrowetting oil-saline/aqueous humor interface, which may change the optical power of the deformable refractive lens formed by the interface. The deformable refractive lens may provide the dynamic optic of the IOL 100.

Figures 2A, 2B:
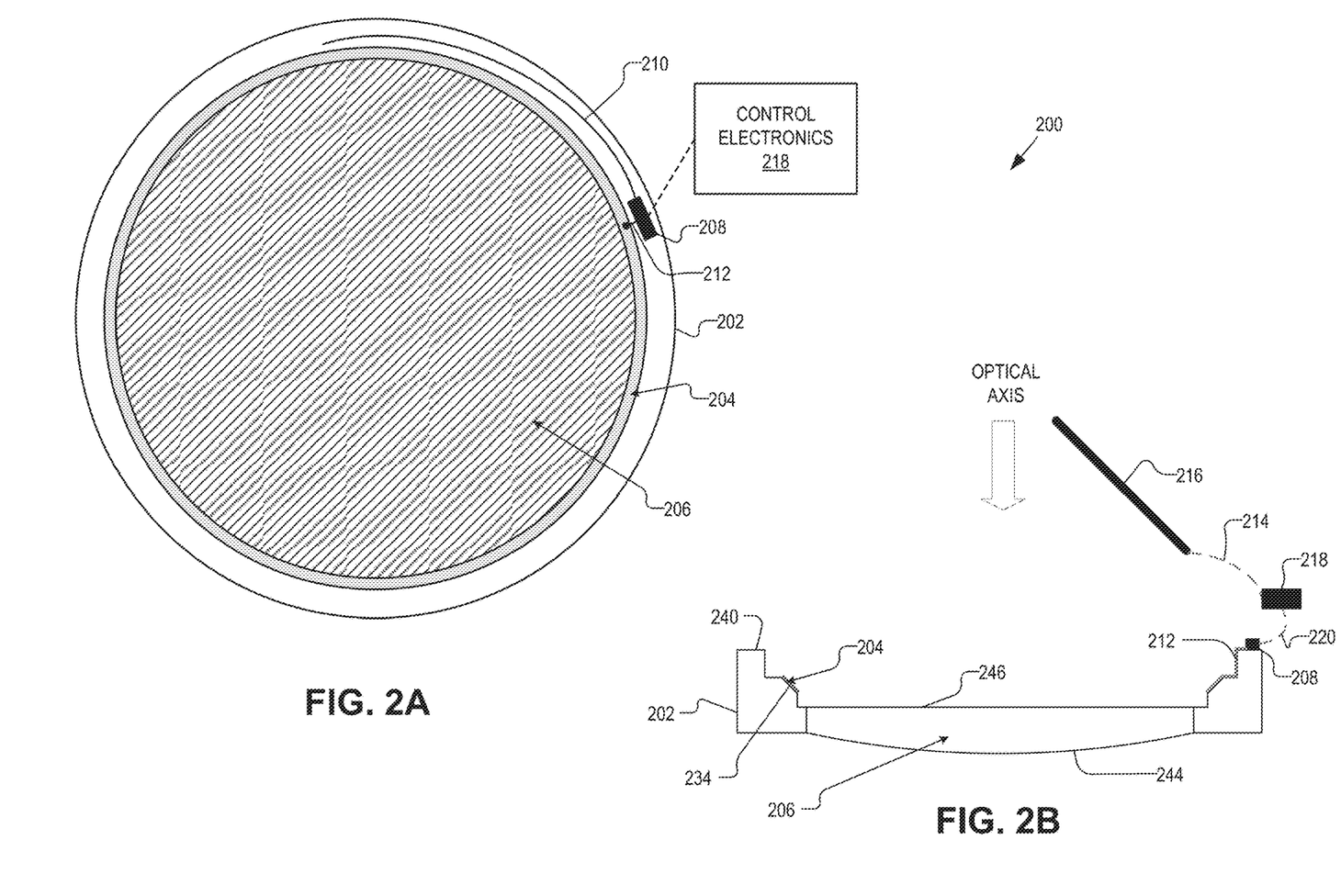
FIGS. 2A and 2B are a plan view illustration of an IOL and a side view illustration of the IOL, respectively, having an open, seal-less construction in accordance with an embodiment of the present disclosure.

FIGS. 2A and 2B are a plan view illustration of an IOL 200 and a side view illustration of the IOL 200, respectively, having an open, seal-less construction in accordance with an embodiment of the present disclosure. The IOL 200 may be similar to the IOL 100 in several aspects, and such similarities may not be discussed with respect to the IOL 200 for sake of brevity. However, the IOL 200 may differ from the IOL 100 in that at least having part of the control electronics, such as control electronics 218, included in/on a separate substrate, which may be implanted in a different area of an eye than are the rest of the IOL 200. For example, the control electronics 218 may be implanted in the sclera of the eye, whereas the IOL 200 may be implanted in the capsular bag.

The illustrated embodiment of the IOL 200 includes a substrate 202, an oil electrode 204 disposed on an inner sidewall 234 of the substrate 202, a first interconnect 212 coupling the oil electrode 204 to first control electronics 208, second control electronics 218 coupled to the first control electronics 208 via a third interconnect 220, and a saline electrode coupled to the second control electronics 218 via a second interconnect 214. In some embodiments, the functions provided by first and second control electronics 208, 218 combined may correspond to the functions provided by the control electronics 108. It should be noted that the control electronics 208 and 218 may be divided into as many separate components as desired, and any number of components are contemplated by the present disclosure.

In some embodiments, the first control electronics 208 may include one or more power sources to provide power, and control logic configured to control accommodation by the dynamic optic. The first control electronics 208 may additionally include one or more communication interfaces to communicate with at least the second control electronics 218. Further, charging circuitry for charging on-board batteries via inductive coupling, for example, may be included in the first control electronics 208. The second control electronics 218 may, in general, include similar functional blocks as the first control electronics 208. However, because the second control electronics 218 may be implanted in a different location, the size of the second control electronics 218 may be less constrained than that of the first control electronics 208. Accordingly, the second control electronics 218 may have larger power storage, and may charge the power supply of the first control electronics 208 as needed.

The control of the IOL 200 may be split between the first and second control electronics 208, 218. For example, the second control electronics 218 may include logic configured to determine when to accommodate and by how much, which may be communicated to the first control electronics 208, which controls the dynamic optic of the IOL 200 accordingly.

The third interconnect 220 may be a physical connection or a wireless connection between the first and second control electronics 208, 218. Similarly, the second interconnect 214 may be a physical connection or a wireless connection.

Figures 3A, 3B:
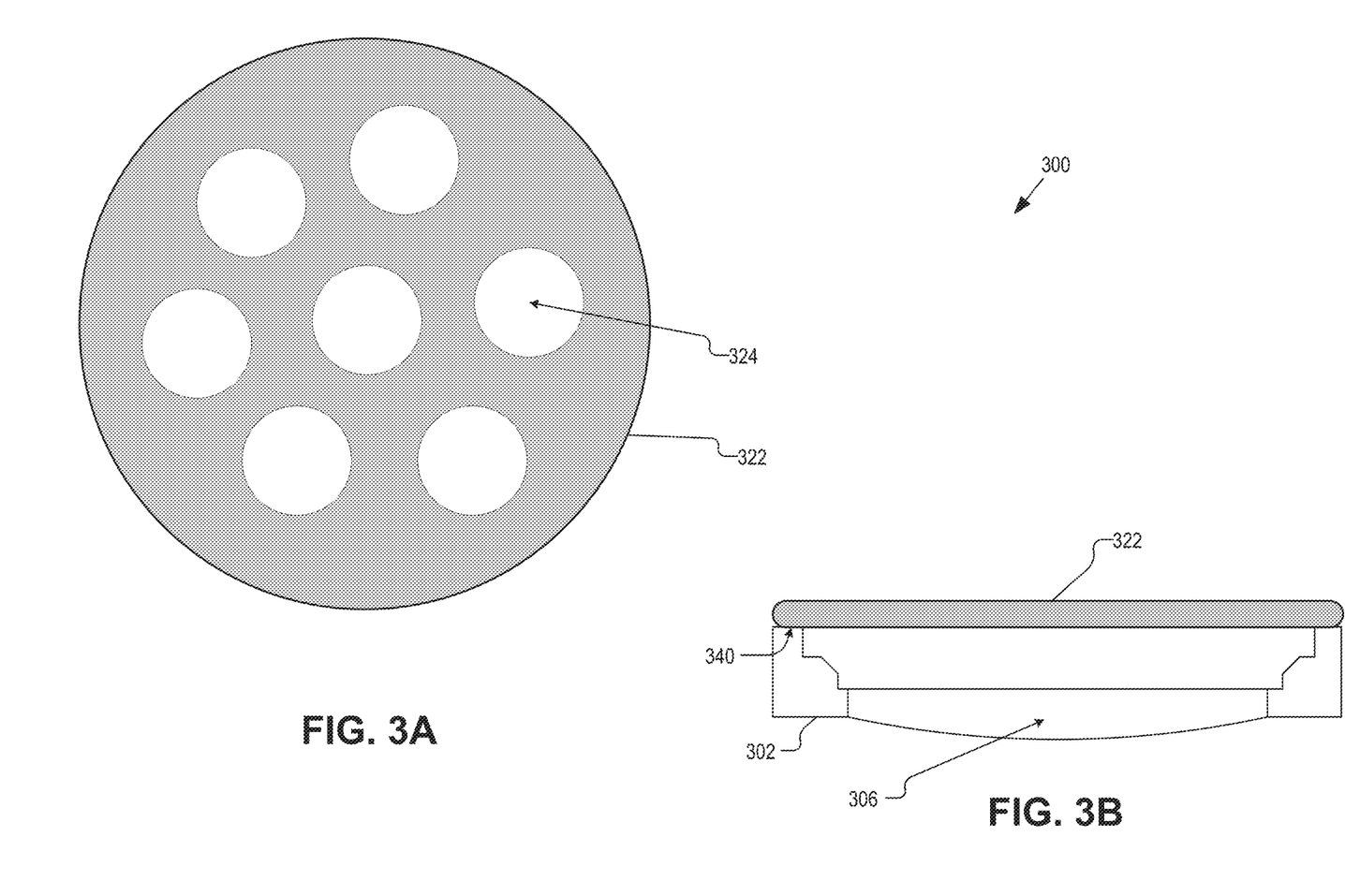
FIGS. 3A and 3B are a plan view illustration of a cover of an IOL, and a side view of the IOL including the cover in accordance with an embodiment of the present disclosure.

FIGS. 3A and 3B are a plan view illustration of a cover 322 of an IOL 300, and a side view of the IOL 300 including the cover 322 in accordance with an embodiment of the present disclosure. The IOL 300 may be an example of the IOL 100 and/or 200. The IOL 300 may be substantially similar to the IOL 100 and/or 200. As such, many of the components are not shown in FIG. 3A or 3B for sake of brevity. The IOL 300 differs from the IOLs 100 and 200 in that a cover 322 may (optionally) be coupled to the substrate 302. However, the cover 322 may have one or more openings formed therethrough that allow for fluidic movement into and out of an inner volume of the IOL 300.

The illustrated embodiment of the IOL 300 includes a substrate 302, an optical window 306 coupled to the substrate 302, and the cover 322 coupled to the substrate 302. The cover 322 may be coupled to an opposite side of the substrate 302 than the optical window 302. For example, the cover 322 may be coupled to a surface 340 of the substrate 302. With regards to the IOL 100 and the IOL 200, the cover 322 may include recesses and/or cutouts to cover and/or surround the control electronics 108 and 208.

The cover 322 may have one or more openings 324 that allow fluid flow in and out of an inner volume of the IOL 300. The inner volume may at least be defined by the inner sidewall, the optical window 306, and the cover 322. The one or more openings 324 may be openings cut or molded into the cover 322, and the number, size, and shape of the one or more openings 324 is a non-limiting aspect of the present disclosure. For example, the one or more openings 324 may be circular, as is shown in FIG. 3A. Further, while the cover 322 is shown as a flat piece that spans across the back of the substrate 302, the cover 322 may be shaped differently, such as hemispherical.

Although a saline electrode is not shown in FIG. 3B, a saline electrode may be included with the IOL 300. In some embodiments, the saline electrode may be disposed inside the inner volume of the IOL 300 or external thereto. In some embodiments, the saline electrode may be integrated into or disposed on one or more surfaces of the cover 322.

The cover 322 may be fastedly attached to the substrate 302, and may be attached thereto post implantation of the rest of the IOL 300. For example, a substrate 302 and optical window 306 assembly may be implanted into an eye, and positioned into a desired location prior to the implantation and attachment of the cover 322. The cover 322 may either be posterior facing (inward facing), or anterior facing (outward facing) after coupling to the substrate 302 and implantation, for example. The cover 322 may snap onto or an adhesive may be used to couple the cover 322 to the substrate 302. In some embodiments, the cover 322 may additionally include a septum allowing for the insertion of a needle. For example, the septum may provide a conduit for a needle to be placed into the inner volume of the IOL 300 for the addition or subtraction of an electrowetting oil.

Figure 4:
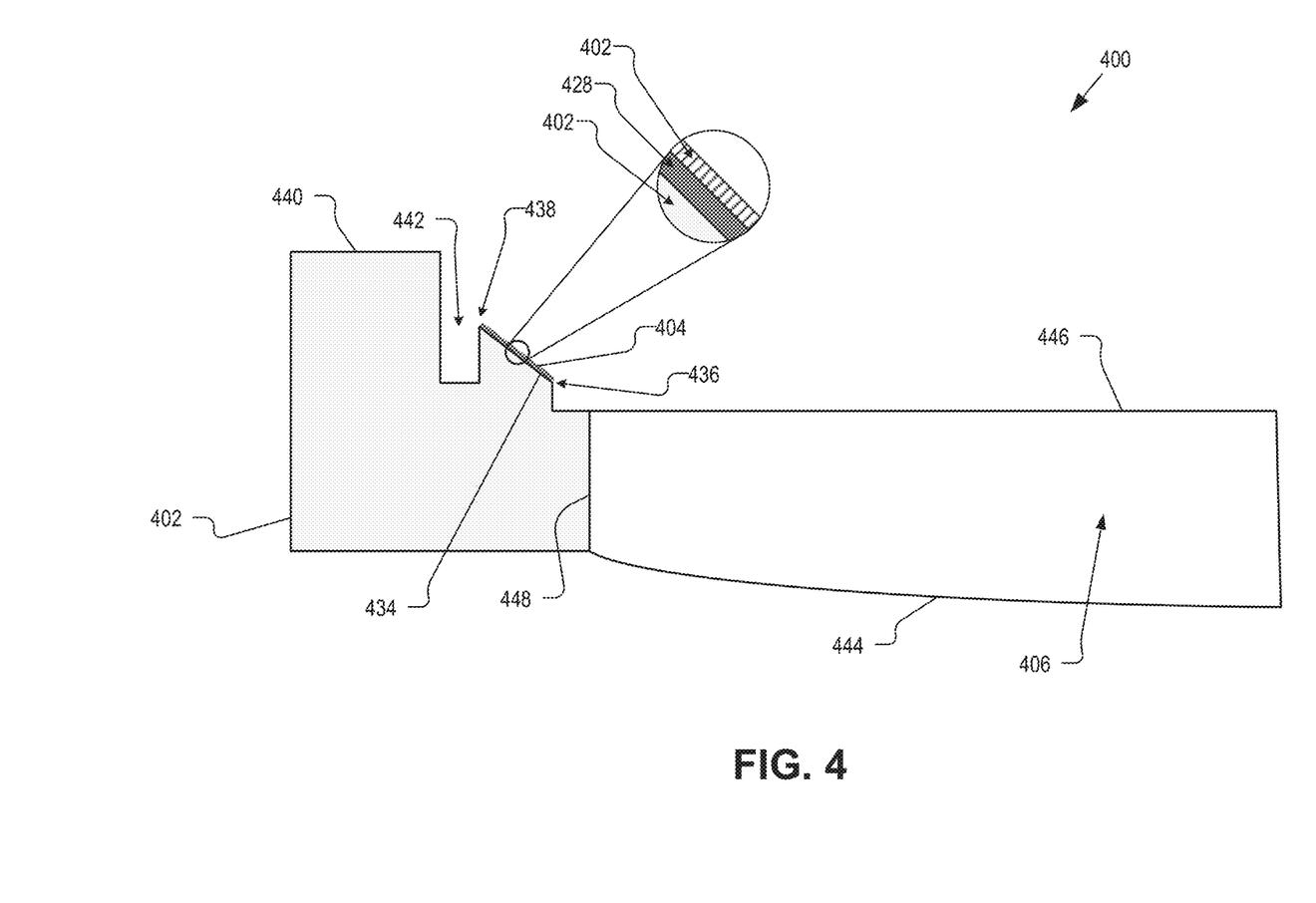
FIG. 4 is an illustrative partial cross-sectional view of an IOL having an open, seal-less construction in accordance with an embodiment of the present disclosure.

FIG. 4 is an illustrative partial cross-sectional view of an IOL 400 having an open, seal-less construction in accordance with an embodiment of the present disclosure. The IOL 400 may be an example of the IOLs 100, 200, and/or 300. The IOL 400 may provide additional detail regarding a substrate, a sidewall, and an oil electrode, for example.

The illustrated embodiment of the IOL 400 includes a substrate 402, an oil electrode 404 formed on an inner sidewall 434, and an optical window 406. The optical window may be coupled to a surface 448 of the substrate 402. For example, the optical window 406 may be inserted into an inner diameter of the substrate 402 associated with the surface 448, and one or more processes may be performed to fixedly coupled the optical window 406 and the substrate 402. Alternatively, the optical window 406 may be integrated with the substrate 402 so that they may be formed in the same mold, for example.

The substrate 402 may include the surface 448, top surface 440, a channel 442, and an inner sidewall 434. The top surface 440 may provide support for mounting electronics, conductive interconnect(s), one or more antennae, and a cover, for example. The surface 448, which may be an inner surface of the substrate 402, may provide, as noted, a location for coupling the optical window in embodiments where the substrate 402 and optical window 406 are separate components. However, in embodiments where the optical window 406 is integrated with the substrate 402, the surface 448 may not be present.

The inner sidewall 434 may be formed at an oblique angle to at least the top surface 440. In some embodiments, the oblique angle may be around 45-degrees. In some embodiments, the inner sidewall 434 may have the form of a conical frustum, which may be at an angle of 45-degrees. The angle of the sidewall 434 with respect to the top surface 440, however, is a non-limiting aspect of the present disclosure, and in general may be based on various other eye and device parameters.

The inner sidewall 434 may provide a surface for an oil electrode, such as the oil electrode 404. The oil electrode 404 may include a thin conductive film 428 and a dielectric layer 426. The thin conductive film 428 may be formed from a transparent or semi-transparent conductor in some embodiments. For example, the thin conductive film 428 may be formed from a conductive polymer or a nanowire mesh, such as silver nanowire. The dielectric layer 426, which may be formed from one or more dielectric layers, may be disposed over the thin conductive film 428. The dielectric layer 426, as noted, may be formed from various parylene substances, aluminum oxide, Teflon AF1600, and the like. The dielectric layer 426 may provide a wetting layer to an electrowetting oil, for example. The wettability of the dielectric layer 426 may be changed based on an amount and polarity of charge applied to the thin conductive film 428.

Additionally, the inner sidewall 434 may be defined by edges 436 and 438. The edges 436 and 438 may alternatively be referred to as "sharps" 436 and 438. The edges 436 and 438 may determine the boundaries that an electrowetting oil may move on the surface of the oil electrode 404. For example, when a charge is applied to the oil electrode 404 that pushes the electrowetting oil away, the electrowetting oil may move away from the oil electrode 404 but stop at, e.g., be bound by, the edge 436. Conversely, when a charge is applied to the oil electrode 404 that attracts the electrowetting oil, the electrowetting oil may move toward and up the oil electrode 404 but stop at, e.g., be bound by, the edge 438. Applying charge to the oil electrode 404 may change the surface properties of the dielectric layer 426 disposed over the thin conductive film 428, for example. The change is surface properties of the dielectric layer 426 may vary the dielectrics wettability with respect to the electrowetting oil, for example, which may cause the electrowetting oil to traverse up and down the surface of the oil electrode 404.

The channel 442 may be formed radially outward of the inner sidewall 434. The channel 442 may be formed in the substrate 402 in order to define the edge 438. Likewise, the drop off from the edge 436 to a surface of the substrate 402 that is flush with the posterior side 446 of the optical window 406 may be formed in the substrate 402 to define the edge 436.

Figure 5:
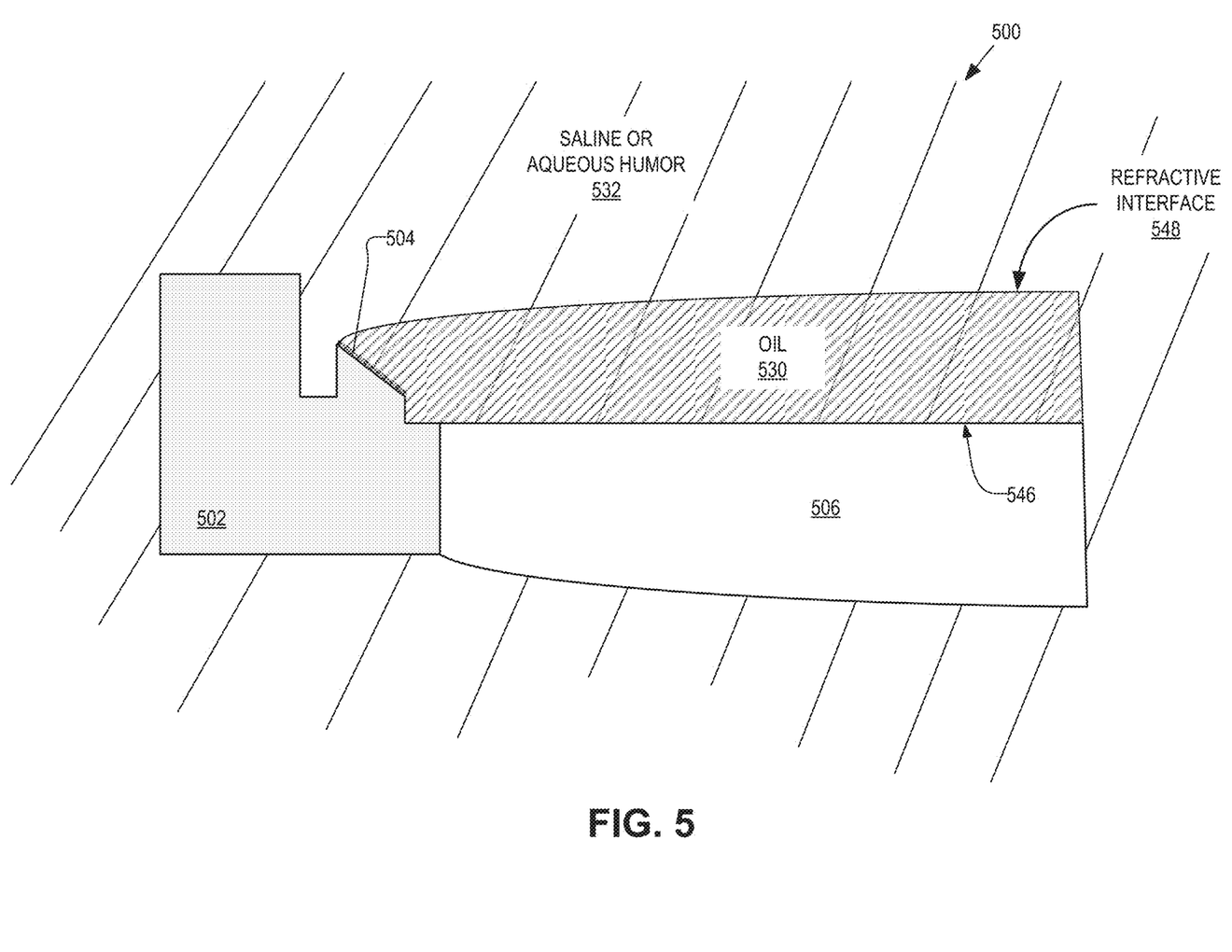
FIG. 5 is an illustrative partial cross-sectional view of an IOL having an open, seal-less construction in accordance with an embodiment of the present disclosure.

FIG. 5 is an illustrative partial cross-sectional view of an IOL 500 having an open, seal-less construction in accordance with an embodiment of the present disclosure. The IOL 500 may be an example of the IOLs 100, 200, 300 and/or 400. The IOL 500 may provide additional detail regarding the oil electrode, an electrowetting oil, and a saline and/or aqueous humor.

The illustrated embodiment of the IOL 500 includes a substrate 502, an oil electrode 504, an optical window 506, an electrowetting oil 530, and saline/aqueous humor 532. The electrowetting oil 530 may be disposed on a posterior side of the IOL 500, and may be adjacent to or in contact with the oil electrode 504 and a posterior side 546 of the optical window 506. The electrowetting oil 530 may be attracted to the surfaces of the oil electrode 504 and the optical window 506 due to surface properties of the same. Additionally, due to the immiscibility of the electrowetting oil 530 and the saline/aqueous humor 532, the electrowetting oil 530 may not disperse into the surrounding fluid, and may instead remain as a single globule of electrowetting oil.

In some embodiments, the electrowetting oil 530 may desirably have a characteristic density roughly equal to the aqueous humor 532. For example, based on the specific gravity of the aqueous humor 532 being around 1.0053, it may be desirable for the electrowetting oil 530 to have a specific gravity of 1.0053±0.003. By matching the density of the electrowetting oil 530 and the aqueous humor 532, the electrowetting oil 530 may be less likely to move around in the eye. If, for example, the density of the electrowetting oil 530 is greater than that of the aqueous humor 532, the electrowetting oil 530 may (slowly) move to the bottom of the eye. Conversely, if the density of the electrowetting oil 530 is less than that of the aqueous humor 532, the electrowetting oil 530 may float to the top of the eye.

In some embodiments, the saline/aqueous humor 532 may be more saline than aqueous humor. For example, during implantation of the IOL 500, the eye may be thoroughly flushed with saline to clean out any debris present due to the implantation procedure. The eye's own fluid, the aqueous humor, may slowly replace the saline, which may be removed from the eye through normal biological processes. As such, the fluid surrounding the IOL 500, including the electrowetting oil 530, may eventually consist mainly of the aqueous humor.

As shown in FIG. 5, a top side of the electrowetting oil 530 stops at a top edge of the oil electrode 504. Additionally, a refractive interface 548 may be formed at the boundary between the electrowetting oil 530 and the saline/aqueous humor 532. The refractive interface 548 provides the dynamic optic for the IOL 500 and the shape of the refractive interface 548 may be changed due to a charge placed on the oil electrode 504 and a saline electrode (not shown), such as the saline electrode 116. For example, as a potential difference between the oil electrode 504 and a saline electrode is changed, by value and/or sign, the electrowetting oil 530 may move up and down the oil electrode 504. The movement of the electrowetting oil 530 up and down the oil electrode 504 may cause the refractive interface 548 in the aperture to change shape, e.g., become less or more spherical/aspherical, which may change an optical power of the dynamic optic. Further, changing the optical power of the dynamic optic may provide accommodation to a user, for example.

Figure 6:
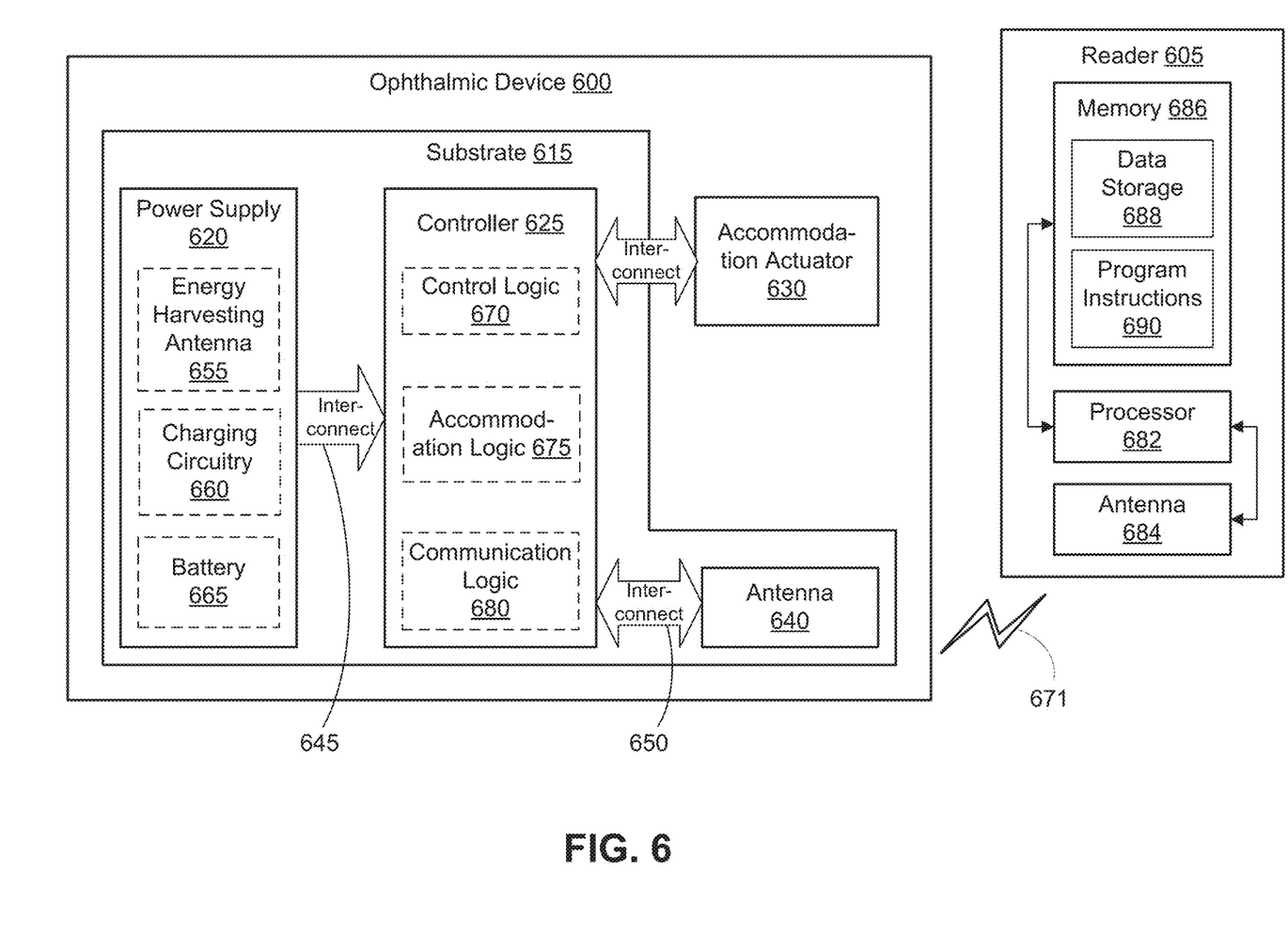
FIG. 6 is a functional block diagram of an IOL including patterned tabs in accordance with an embodiment of the present disclosure.

FIG. 6 is a functional block diagram of an IOL 600 including patterned tabs in accordance with an embodiment of the present disclosure. IOL 600 may be an implantable device. In the depicted embodiment, IOL 600 includes a substrate 615 embedded that provides a mounting surface for a power supply 620, a controller 625, an antenna 640, and various interconnects 645 and 650. The substrate 615 and the associated electronics may be one implementation of the substrate 102/202 and the control electronics 108/208/218. The illustrated embodiment of power supply 620 includes an energy harvesting antenna 655, charging circuitry 660, and a battery 665. The illustrated embodiment of controller 625 includes control logic 670, accommodation logic 675, and communication logic 680.

Power supply 620 supplies operating voltages to the controller 625 and/or the accommodation actuator 630. Antenna 640 is operated by the controller 625 to communicate information to and/or from IOL 600. In the illustrated embodiment, antenna 640, controller 625, power supply 620, and at least part of the accommodation actuator 630, e.g., the oil electrode, are disposed on/in substrate 615. The other part of the accommodation actuator 630, e.g., a saline electrode, may be disposed elsewhere within the eye, but may be in electrical communication with the controller 625. However, in other embodiments, the various pieces of circuitry and devices contained in ophthalmic device 600 may be disposed in/on substrate 615 or on a separate substrate, depending on the specific design of ophthalmic device 600. For example, in one embodiment, additional control circuitry may be disposed on a separate substrate, which may be implanted in a different part of the eye, such as the sclera.

Substrate 615 includes one or more surfaces suitable for mounting controller 625, power supply 620, and antenna 640. Substrate 615 can be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide or silver nanowire mesh) can be patterned on substrate 615 to form circuitry, electrodes, etc. For example, antenna 640 can be formed by depositing a pattern of gold or another conductive material on substrate 615. Similarly, interconnects 645 and 650 can be formed by depositing suitable patterns of conductive materials on substrate 615. A combination of resists, masks, and deposition techniques can be employed to pattern materials on substrate 615. Substrate 615 can be a relatively rigid material, such as polyethylene terephthalate (PET) or another material sufficient to structurally support the circuitry and/or electronics within enclosure material 610. IOL 600 can alternatively be arranged with a group of unconnected substrates rather than a single substrate 615. For example, controller 625 and power supply 620 can be mounted to one substrate 615, while antenna 640 is mounted to another substrate 615 and the two can be electrically connected via interconnects. 6

Substrate 615 can be shaped as a flattened ring with a radial width dimension sufficient to provide a mounting platform for the embedded electronic components. Substrate 615 can have a thickness sufficiently small to allow substrate 615 to 6 adversely influence the profile and/or volume of IOL 600. Substrate 615 can have a thickness sufficiently large to provide structural stability suitable for supporting the electronics mounted thereon.

In the illustrated embodiment, power supply 620 includes a battery 665 to power the various embedded electronics, including controller 625. Battery 665 may be inductively charged by charging circuitry 660 and energy harvesting antenna 655. In one embodiment, antenna 640 and energy harvesting antenna 655 are independent antennae, which serve their respective functions of energy harvesting and communications. In another embodiment, energy harvesting antenna 655 and antenna 640 are the same physical antenna that are time shared for their respective functions of inductive charging and wireless communications with reader 605. Additionally or alternatively, power supply 620 may include a photovoltaic cell to capture energy from incoming ultraviolet, visible, and/or infrared radiation. Furthermore, an inertial power scavenging system can be included to capture energy from ambient vibrations.

Charging circuitry 660 may include a rectifier/regulator to condition the captured energy for charging battery 665 or directly power controller 625 without battery 665. Charging circuitry 660 may also include one or more energy storage devices to mitigate high frequency variations in energy harvesting antenna 655. For example, one or more energy storage devices (e.g., a capacitor, an inductor, etc.) can be connected to function as a low-pass filter.

Controller 625 contains logic to choreograph the operation of the other embedded components. Control logic 670 controls the general operation of IOL 600, including providing a logical user interface, power control functionality, etc. Accommodation logic 675 includes logic for receiving signals from sensors monitoring the orientation of the eye, determining the current gaze direction or focal distance of the user, and manipulating accommodation actuator 630 (focal distance of the contact lens) in response to these physical cues. The auto-accommodation can be implemented in real-time based upon feedback from gaze tracking, or permit the user to select specific accommodation regimes (e.g., near-field accommodation for reading, far-field accommodation for regular activities, etc.). Communication logic 680 provides communication protocols for wireless communication with reader 605 via antenna 640. In one embodiment, communication logic 680 provides backscatter communication via antenna 640 when in the presence of an electromagnetic field 671 output from reader 605. In one embodiment, communication logic 680 operates as a smart wireless radio-frequency identification (RFID) tag that modulates the impedance of antenna 640 for backscatter wireless communications. The various logic modules of controller 625 may be implemented in software/firmware executed on a general purpose microprocessor, in hardware (e.g., application specific integrated circuit), or a combination of both.

IOL 600 may include various other embedded electronics and logic modules. For example, a light source or pixel array may be included to provide visible feedback to the user. An accelerometer or gyroscope may be included to provide positional, rotational, directional or acceleration feedback information to controller 625.

The illustrated embodiment also includes reader 605 with a processor 682, an antenna 684, and memory 686. Memory 686 in reader 605 includes data storage 688 and program instructions 690. As shown reader 605 may be disposed outside of IOL 600, but may be placed in its proximity to charge IOL 600, send instructions to IOL 600, and/or extract data from IOL 600. In one embodiment, reader 605 may resemble a conventional contact lens holder that the user places IOL 600 in at night to charge, extract data, clean the lens, etc.

External reader 605 includes an antenna 684 (or group of more than one antennae) to send and receive wireless signals 671 to and from IOL 600. External reader 605 also includes a computing system with a processor 682 in communication with a memory 686. Memory 686 is a non-transitory computer-readable medium that can include, without limitation, magnetic disks, optical disks, organic memory, and/or any other volatile (e.g., RAM) or non-volatile (e.g., ROM) storage system readable by the processor 682. Memory 686 can include a data storage 688 to store indications of data, such as data logs (e.g., user logs), program settings (e.g., to adjust behavior of IOL 600 and/or external reader 605), etc. Memory 686 can also include program instructions 690 for execution by processor 682 to cause the external reader 605 to perform processes specified by the instructions 690. For example, program instructions 690 can cause external reader 605 to provide a user interface that allows for retrieving information communicated from IOL 600 or allows transmitting information to IOL 600 to program or otherwise select operational modes of IOL 600. External reader 405 can also include one or more hardware components for operating antenna 684 to send and receive wireless signals 671 to and from IOL 600.

External reader 605 can be a smart phone, digital assistant, or other portable computing device with wireless connectivity sufficient to provide the wireless communication link 671. External reader 605 can also be implemented as an antenna module that can be plugged into a portable computing device, such as in an embodiment where the communication link 671 operates at carrier frequencies not commonly employed in portable computing devices. In some instances, external reader 605 is a special-purpose device configured to be worn relatively near a wearer's eye to allow the wireless communication link 671 to operate with a low power budget. For example, the external reader 605 can be integrated in a piece of jewelry such as a necklace, earing, etc. or integrated in an article of clothing worn near the head, such as a hat, headband, etc.

Figure 7:
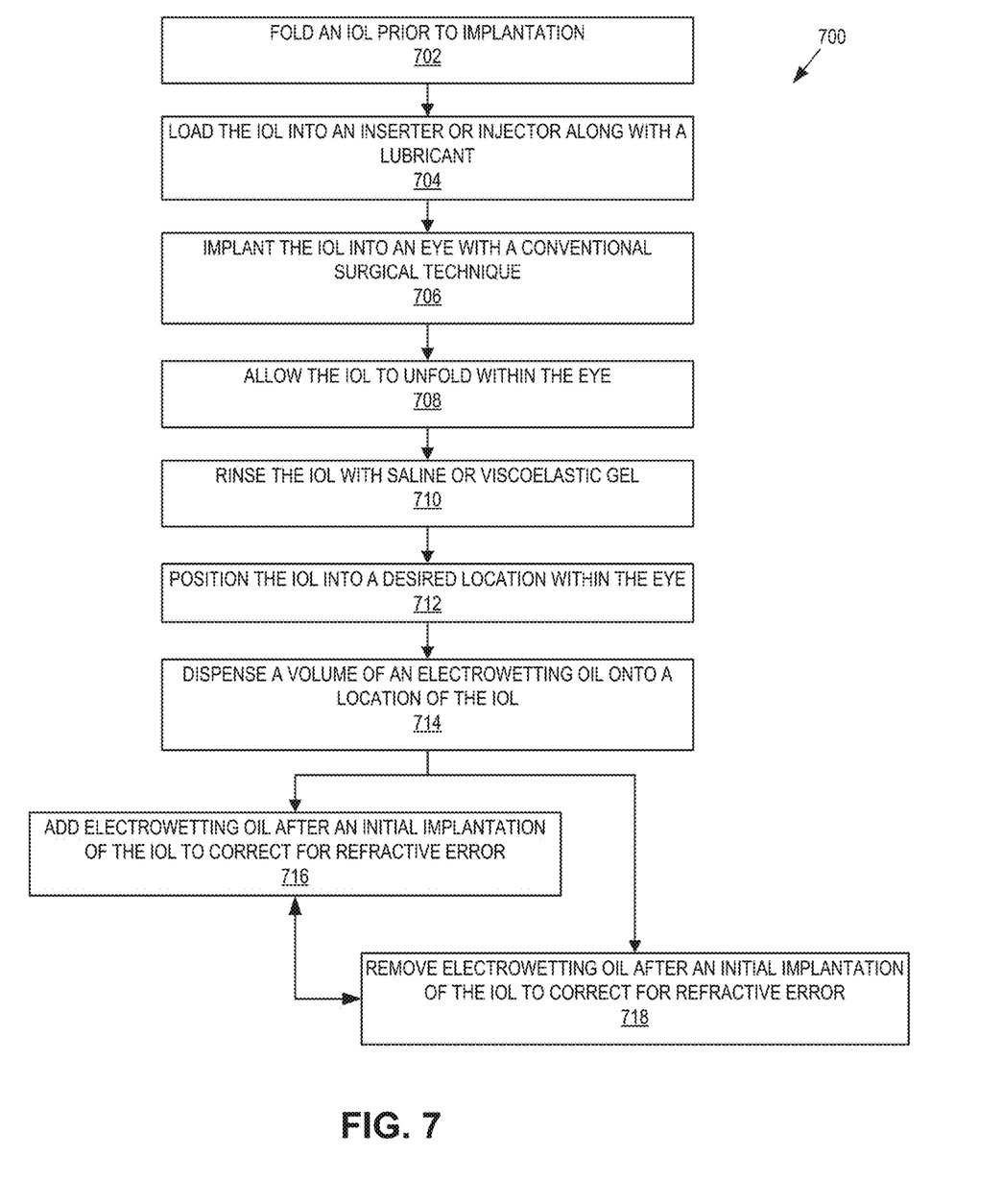
FIG. 7 is an example IOL implantation process in accordance with an embodiment of the present disclosure.

FIG. 7 is an example IOL implantation process 700 in accordance with an embodiment of the present disclosure. The process 700 is an example process for implanting an IOL, such as the IOL 100 or 200. The process 700 may be performed by an eye care physician. In contrast to implanting a conventional IOL, the implantation of an IOL 100 or 200 includes the steps of injecting an electrowetting oil into a desired location of the IOL after the body of the IOL has been implanted and positioned within an eye.

The process 700 may begin at process block 702 with folding an IOL prior to implantation. For example, an IOL 100 or 200 may be folded or rolled to reduce its size and prepare it for insertion into the eye. The process block 702 may be followed by the process block 704, which includes loading the IOL into an inserter or injector. Along with loading the IOL into the inserter/injector, one or more lubricants may also be applied to the IOL and or the inserter/injector. In some embodiments, the act of loading the IOL into the inserter/injector may result in the folding and/or rolling of the IOL.

Process block 704 may be followed by process block 706, which includes implanting the IOL into an eye with any conventional surgical technique. The IOL may be implanted into any desirable location of the eye, such as the posterior chamber, anterior chamber, or the secular bag. For example, a small incision, 2 to 5 mm, may be made in the eye, and another in the capsular bag. Using the injector, to continue the example, the rolled and/or folded IOL may be inserted through the incisions and implanted into the capsular bag. It should be noted that the crystalline lens material that was in the capsular bag may be removed before the IOL is implanted.

Process block 706 may be followed by process block 708, which includes allowing the IOL to unfold within the eye. The IOL may, for example, unfold and/or unroll into a desired geometry. The process block 710 may follow the process block 708 with rinsing the IOL with saline or viscoelastic gel. The rinsing of the IOL post implantation may be performed to remove any debris and left over crystalline material from the capsular bag, for example. Upon completion of the rinsing step, the saline or viscoelastic gel used for the rinse may remain in the capsular bag. The remaining fluid, however, may slowly be replaced by the eye's aqueous humor.

The process block 710 may be followed by the process block 712, which includes positioning the IOL into a desired location within the eye. For example, the IOL may be positioned into the ultimate location for utility, e.g., providing vision correction and accommodation for the user. The positioning may include finely positioning the optical axis of the optical window, such as the optical window 106/206, to be in line with and parallel with the optical axis of the eye. The positioning of the IOL may be an iterative process and may include sequential minor adjustments and observations by the physician to obtain the desired position. It should be noted that process block 710 may be continually performed and/or periodically performed during process blocks 706, 708, and 712.

Process block 712 may be followed by process block 714, which includes dispensing a volume of an electrowetting oil onto a location of the IOL. For example, a volume of the electrowetting oil may be dispensed onto a posterior surface of the optical window of the IOL and allowed to flow and contact an oil electrode encompassing the optical window. The volume of the electrowetting oil may be dependent upon a desired optical power. The electrowetting oil may be dispensed through a needle, for example, the physician inserts into the eye and in a posterior position of the implanted IOL. In some embodiments, the process block 714 may be done in the same operation as the implantation of the IOL. In other embodiments, however, the process block 714 may be performed at a later date and during a subsequent operation. The dispensing of the electrowetting oil will complete the implantation of the IOL by forming the refractive interface between the electrowetting oil and saline and/or aqueous humor.

Process block 714 may be followed by either optional process block 716 or 718. Process blocks 716 and 718 may be optional because they may be performed if the volume of electrowetting oil that is currently in the eye does not provide the desired optical power. For example, if the initial volume of electrowetting oil was too little, which may generate a dynamic lens with less optical power than needed, then process block 716 may be performed in which more electrowetting oil is added. Conversely, if the initial volume of electrowetting oil was too much, which may generate a dynamic lens with more optical power than needed, then process block 718 may be performed in which electrowetting oil is removed from the IOL. In both processes, a needle may be inserted into the eye and in contact with the electrowetting oil in the posterior of the IOL. To add oil, a desired volume of oil may be previously added to the needle and then dispensed into the current oil. To remove oil, a desired amount of oil may be syphoned into the needle. One or both of the process blocks 716 and 718 may be periodically performed due to changes in the user's prescription, for example.

After implantation of the IOL, operation of the IOL may be verified. For example, the eye physician may trigger the IOL to accommodate, such as through an external reader. While the IOL is triggered, the physician may observe movement of the oil-saline or oil-aqueous humor interface on an oil electrode. At this time, the eye physician may additionally determine if the optical power of the IOL satisfies the patient's prescription as well. If not, then one of process block 716 or 718 may be repeated.

The order in which some or all of the process blocks appear in process 700 should not be deemed limiting. Rather, one of ordinary skill in the art having the benefit of the present disclosure will understand that some of the process blocks may be executed in a variety of orders not illustrated, or even in parallel.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An intraocular lens, comprising:
    an annular substrate including an oil electrode disposed in or on an inner sidewall of the annular substrate to electrostatically manipulate a volume of electrowetting oil, wherein the oil electrode is annular shaped and encircles an aperture through the annular substrate;
    an optical window coupled to the annular substrate and extending across the aperture, wherein a side of the optical window and the inner sidewall of the annular substrate collectively define a region for constraining the volume of electrowetting oil; and
    a saline electrode coupled to the annular substrate, the saline electrode positionable within an aqueous humor of an eye upon implantation.

2. The intraocular lens of claim 1, wherein the volume of electrowetting oil is dispensed onto a posterior surface of the optical window and the oil electrode after implantation of the intraocular lens into an eye.

3. The intraocular lens of claim 2, wherein an interface between the electrowetting oil and the aqueous humor of the eye is formed after the electrowetting oil is disposed on the surface of the optical window and the oil electrode.

4. The intraocular lens of claim 3, wherein the interface forms a refractive optic.

5. The intraocular lens of claim 1, further comprising:
    control electronics disposed on the annular substrate, the control electronics coupled to the oil electrode and the saline electrode.

6. The intraocular lens of claim 5, wherein the control electronics control a dynamic optic formed from a refractive interface, the refractive interface formed at an interface of the electrowetting oil disposed on a surface of the optical window and the oil electrode after implantation of the intraocular lens into an eye and an aqueous humor of the eye.

7. The intraocular lens of claim 1, wherein a density of the electrowetting oil is equivalent to a density of the aqueous humor.

8. An implantable ophthalmic device, comprising:
    an annular substrate having a first electrode disposed on an inner sidewall of the annular substrate, wherein the first electrode is annular shaped and encircles an aperture through the annular substrate;
    a second electrode coupled to the annular substrate, wherein the second electrode is positionable within an aqueous humor of an eye after the implantable device has been implanted in the eye;
    control electronics disposed on the annular substrate and coupled to the first and second electrodes; and
    an optical window coupled to the annular substrate and extending across the aperture, wherein a side of the optical window and the inner sidewall of the annular substrate collectively define an area for receiving an electrowetting oil.

9. The implantable ophthalmic device of claim 8, further comprising:
    electrowetting oil disposed in the area for receiving the electrowetting oil, and
    wherein a dynamic optic is formed at an interface of the oil opposite the optical window.

10. The implantable ophthalmic device of claim 9, wherein, when the implantable ophthalmic device is implanted in the eye, the control electronics provide a charge to the first and second electrodes to establish a potential difference between the first and second electrodes to change a shape of the interface between the electrowetting oil and the aqueous humor.

11. The implantable ophthalmic device of claim 10, wherein the change in shape of the interface between the electrowetting oil and the aqueous humor is a dynamic optic.

12. The implantable ophthalmic device of claim 8, wherein the second electrode is placed anywhere inside the eye in contact with the aqueous humor when the ophthalmic device is implanted into the eye.

13. The implantable ophthalmic device of claim 8, further comprising a cover coupled to the annular-shaped substrate on an opposing side from the optical window, the cover including one or more openings to expose an inner volume to at least the aqueous humor of the eye after the ophthalmic device is implanted in the eye.

14. The implantable ophthalmic device of claim 8, wherein the inner sidewall surrounds an aperture of the annular substrate, and wherein the inner sidewall has a shape of a 45-degree conical frustrum.

15. The implantable ophthalmic device of claim 8, wherein the first electrode comprises a thin conductive film disposed on the inner sidewall and a dielectric layer disposed over the thin conductive film.

16. The implantable ophthalmic device of claim 8, wherein the ophthalmic device is configured to be implantable into one of a capsular bag, an anterior chamber, or a posterior chamber of the eye.

17. The intraocular lens of claim 1, wherein the saline electrode is not disposed on the annular substrate but is connected to the annular substrate via a wire interconnect which facilitates positioning the saline electrode away from the annular substrate within the aqueous humor of the eye.

* * * * *